US008632755B2

(12) United States Patent
Scavone et al.

(10) Patent No.: US 8,632,755 B2
(45) Date of Patent: Jan. 21, 2014

(54) CONSUMER NOTICEABLE IMPROVEMENT IN WETNESS PROTECTION

(75) Inventors: Timothy Alan Scavone, Loveland, OH (US); George Endel Deckner, Cincinnati, OH (US); Zerlina Guzdar Dubois, Mason, OH (US); Theresa Louise Johnson, South Lebanon, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 444 days.

(21) Appl. No.: 11/712,775

(22) Filed: Mar. 1, 2007

(65) Prior Publication Data

US 2007/0248553 A1    Oct. 25, 2007

Related U.S. Application Data

(63) Continuation-in-part of application No. 11/418,635, filed on May 5, 2006, which is a continuation-in-part of application No. 11/132,823, filed on May 19, 2005.

(51) Int. Cl.
*A61K 8/00* (2006.01)
*A61K 8/26* (2006.01)
*A61K 9/00* (2006.01)
*A61K 8/02* (2006.01)

(52) U.S. Cl.
USPC ............. 424/65; 424/68; 424/400; 424/401

(58) Field of Classification Search
USPC ..................... 424/65, 68, 400, 401
See application file for complete search history.

(56) References Cited

U.S. PATENT DOCUMENTS

| 4,803,195 | A | 2/1989 | Holzner |
|---|---|---|---|
| 5,135,747 | A | 8/1992 | Faryniarz et al. |
| 5,176,903 | A | 1/1993 | Goldberg et al. |
| 5,378,468 | A | 1/1995 | Suffis et al. |
| 5,380,707 | A | 1/1995 | Barr et al. |
| 5,508,259 | A | 4/1996 | Holzner et al. |
| 5,626,856 | A | 5/1997 | Berndt |
| 5,711,941 | A | 1/1998 | Behan et al. |
| 5,780,020 | A | 7/1998 | Petersen et al. |
| 5,861,144 | A | 1/1999 | Peterson et al. |
| 5,861,146 | A | 1/1999 | Peterson et al. |
| 5,874,067 | A | 2/1999 | Lucas et al. |
| 5,879,666 | A | 3/1999 | Lucas et al. |
| 5,882,638 | A | 3/1999 | Dodd et al. |
| 5,885,599 | A | 3/1999 | Peterson et al. |
| 5,897,855 | A | 4/1999 | Trinh et al. |
| 5,932,198 | A | 8/1999 | Goldman et al. |
| 6,036,964 | A | 3/2000 | Guenin et al. |
| 6,110,449 | A * | 8/2000 | Bacon et al. ............. 424/65 |
| 6,123,932 | A | 9/2000 | Guskey et al. |
| 6,150,542 | A | 11/2000 | Acuna et al. |
| 6,165,452 | A | 12/2000 | Boden et al. |
| 6,180,121 | B1 | 1/2001 | Guenin et al. |
| 6,187,301 | B1 * | 2/2001 | Scavone et al. ............. 424/65 |
| 6,306,818 | B1 | 10/2001 | Anderson et al. |
| 6,352,688 | B1 | 3/2002 | Scavone et al. |
| 6,375,938 | B1 | 4/2002 | Clothier, Jr. et al. |
| 6,403,071 | B1 | 6/2002 | Scavone et al. |
| 6,432,392 | B1 * | 8/2002 | Ashcroft et al. ............. 424/68 |
| 6,495,097 | B1 | 12/2002 | Streit et al. |
| 6,495,149 | B1 | 12/2002 | Scavone et al. |
| 6,509,010 | B2 | 1/2003 | Beck et al. |
| 6,793,915 | B1 | 9/2004 | Guenin et al. |
| 6,805,855 | B2 | 10/2004 | Mattai et al. |
| 6,835,373 | B2 | 12/2004 | Kolodzik et al. |
| 7,067,152 | B2 | 6/2006 | Shefer et al. |
| 2003/0049290 | A1 | 3/2003 | Jha et al. |
| 2003/0087776 | A1 | 5/2003 | Heltovics et al. |
| 2003/0119713 | A1 | 6/2003 | Heltovics et al. |
| 2003/0165447 | A1 | 9/2003 | Scavone et al. |
| 2003/0194416 | A1 | 10/2003 | Shefer et al. |
| 2003/0198680 | A1 | 10/2003 | Shefer et al. |
| 2003/0198860 | A1 | 10/2003 | Yasumoto |
| 2003/0211125 | A1 | 11/2003 | Heltovics et al. |
| 2003/0230205 | A1 | 12/2003 | Mutschler |
| 2003/0232025 | A1 | 12/2003 | Colwell et al. |

(Continued)

FOREIGN PATENT DOCUMENTS

| EP | 0535942 A3 | 4/1993 |
|---|---|---|
| EP | 0535942 B1 | 2/1999 |

(Continued)

OTHER PUBLICATIONS

Merriam-Webster's Collegiate Dictionary, 1996, Tenth Edition, 3 Page.*
U.S. Appl. No. 11/712,616, filed Mar. 1, 2007, Scavone et al.
USPTO Office Action rejections/objections U.S. Appl. No. 11/132,823; 14 pages.
USPTO Office Action rejections/objections U.S. Appl. No. 11/418,635; 14 pages.
USPTO Office Action rejections/objections U.S. Appl. No. 11/132,824; 14 pages.
USPTO Office Action rejections/objections U.S. Appl. No. 11/418,607; 17 pages.

(Continued)

*Primary Examiner* — Abigail Fisher

(57) ABSTRACT

Antiperspirant compositions comprising: (a) from about 0.1% to about 30% by weight of the composition, of a high-efficacy antiperspirant active; (b) from about 0.1% to about 35% by weight of the composition, of a thickening agent; (c) from about 10% to about 99% by weight of the composition, of an anhydrous liquid carrier; (d) from about 5 ppm to about 20% by weight of the composition, of a primary fragrance; and (e) from at least about 5 ppm by weight of the composition, of a secondary fragrance that is distinct from the primary fragrance and is included in a surfactant-free, water-releasable matrix, which renders the secondary fragrance within the matrix substantially odorless prior to aqueous activation, wherein the antiperspirant composition is substantially devoid of a malodor reducing agent.

14 Claims, No Drawings

(56) References Cited

U.S. PATENT DOCUMENTS

| | | | |
|---|---|---|---|
| 2004/0001891 A1 | 1/2004 | Smith et al. |
| 2004/0091435 A1 | 5/2004 | Shefer et al. |
| 2004/0109833 A1 | 6/2004 | Tang et al. |
| 2004/0175346 A1 | 9/2004 | Guenin et al. |
| 2004/0175404 A1 | 9/2004 | Shefer et al. |
| 2004/0202632 A1 | 10/2004 | Gott et al. |
| 2005/0003975 A1 | 1/2005 | Browne et al. |
| 2006/0263311 A1 | 11/2006 | Scavone et al. |
| 2006/0263312 A1 | 11/2006 | Scavone et al. |
| 2006/0263313 A1 | 11/2006 | Scavone et al. |
| 2006/0292098 A1 | 12/2006 | Scavone et al. |
| 2007/0248552 A1 | 10/2007 | Scavone et al. |
| 2007/0248553 A1 | 10/2007 | Scavone et al. |

FOREIGN PATENT DOCUMENTS

| | | |
|---|---|---|
| EP | 0965326 A1 | 12/1999 |
| EP | 0816322 B1 | 3/2003 |
| EP | 0966258 B1 | 5/2003 |
| JP | 2001316219 A | 11/2001 |
| WO | WO 98/18439 | 5/1998 |
| WO | WO 98/56340 | 12/1998 |
| WO | WO 03/088933 A1 | 10/2003 |
| WO | WO 2004/000254 A1 | 12/2003 |
| WO | WO 2004/000255 A1 | 12/2003 |
| WO | WO2004/078154 A1 | 9/2004 |

OTHER PUBLICATIONS

USPTO Office Action rejections/objections U.S. Appl. No. 11/712,616; 19 pages.
The most current USPTO Office Action rejections/objections with mail date Nov. 13, 2008 U.S. Appl. No. 11/132,823; 29 pages.
The most current USPTO Office Action rejections/objections with mail date Nov. 11, 2008 U.S. Appl. No. 11/418,635; 24 pages.
The most current USPTO Office Action rejections/objections with mail date Nov. 14, 2008 U.S. Appl. No. 11/132,824; 32 pages.
The most current USPTO Office Action rejections/objections with mail date Jan. 7, 2009 U.S. Appl. No. 11/418,607; 17 pages.
The most current USPTO Office Action rejections/objections with mail date Dec. 15, 2009 U.S. Appl. No. 11/712,616; 13 pages.
The most current USPTO Office Action rejections/objections with mail date Feb. 24, 2009 U.S. Appl. No. 11/418,607; 12 pages.
The most current USPTO Office Action rejections/objections with mail date Feb. 20, 2009 U.S. Appl. No. 11/712,616; 11 pages.
Office Action pertaining to U.S. Appl. No. 11/132,823 dated Sep. 25, 2007.
Office Action pertaining to U.S. Appl. No. 11/132,823 dated Jan. 30, 2008.
Office Action pertaining to U.S. Appl. No. 11/132,823 dated Apr. 28, 2009.
Office Action pertaining to U.S. Appl. No. 11/132,823 dated Sep. 28, 2009.
Office Action pertaining to U.S. Appl. No. 11/418,635 dated Sep. 25, 2007.
Office Action pertaining to U.S. Appl. No. 11/418,635 dated Jan. 30, 2008.
Office Action pertaining to U.S. Appl. No. 11/418,635 dated May 11, 2009.
Office Action pertaining to U.S. Appl. No. 11/418,635 dated Sep. 25, 2009.
Office Action pertaining to U.S. Appl. No. 11/132,824 dated Sep. 25, 2007.
Office Action pertaining to U.S. Appl. No. 11/132,824 dated Apr. 29, 2009.
Office Action pertaining to U.S. Appl. No. 11/132,824 dated Sep. 25, 2009.
Office Action pertaining to U.S. Appl. No. 11/418,607 dated Sep. 25, 2007.
Office Action pertaining to U.S. Appl. No. 11/418,607 dated Jan. 30, 2008.
Office Action pertaining to U.S. Appl. No. 11/418,607 dated Jul. 2, 2008.
Office Action pertaining to U.S. Appl. No. 11/418,607 dated Dec. 28, 2009.
Office Action pertaining to U.S. Appl. No. 11/712,616 dated Jul. 2, 2008.
Office Action pertaining to U.S. Appl. No. 11/712,616 dated Dec. 15, 2008.
Office Action pertaining to U.S. Appl. No. 11/712,616 dated Oct. 6, 2009.
PCT/US2006/016093 International Search Report dated Aug. 11, 2006.
PCT/US2006/016092 International Search Report dated Oct. 5, 2006.
International Search Report PCT/US2006/016092 with Written Opinion of the International Searching Authority, mailing date Oct. 5, 2006, 12 pages.
International Search Report PCT/US2006/016093 with Written Opinion of the International Searching Authority, mailing date Aug. 11, 2006, 12 pages.
Chemical Abstracts Registry entry for Amberonne, accessed on Feb. 4, 2011.
Labows, J. N. et al. "Axillary Odor Determination, Formation, and Control" in Antiperspirants and Deodorants, $2^{nd}$ edition, Karl Laden, editor, Marcel Dekker, Inc.: New York, 1999, pp. 59-82.

* cited by examiner

US 8,632,755 B2

CONSUMER NOTICEABLE IMPROVEMENT IN WETNESS PROTECTION

CROSS REFERENCE TO RELATED APPLICATION

This application is a continuation-in-part of U.S. application Ser. No. 11/418,635, filed May 5, 2006, which is a continuation-in-part of U.S. application Ser. No. 11/132,823, filed May 19, 2005.

TECHNICAL FIELD

The present invention relates to antiperspirant compositions that provide to the consumer noticeable improvements in wetness protection via fragrance character shifts.

BACKGROUND OF THE INVENTION

Many different antiperspirant products are known for use in controlling or inhibiting underarm perspiration wetness and odor. These products are available in a variety of product forms such as solid sticks, soft solids or creams, roll-on liquids and aerosol or non-aerosol sprays. Most of these products have a base formula that contains an antiperspirant active such as an aluminum and or zirconium salt, a suspending or thickening agent, and a suitable liquid carrier. Many antiperspirant products are formulated to provide good wetness and odor protection. It has become increasingly difficult, however, to provide improvements in wetness protection that consumers notice. Even when substantial improvements in clinical wetness protection are provided, consumers may not see or notice the improvement.

Surprisingly, it has now been found that by providing high clinical efficacy antiperspirants in combination with a malodor reducing agent and a fragrance character shifting agent, consumers can perceive and appreciate improved wetness protection. The present invention provides high clinical efficacy antiperspirant compositions that deliver consumer-perceived improvement in wetness protection.

SUMMARY OF THE INVENTION

In accordance with one of the preferred embodiments, there has now been provided an antiperspirant composition comprising: (a) from about 0.1% to about 30% by weight of the composition, of a high-efficacy antiperspirant active; (b) from about 0.1% to about 35% by weight of the composition, of a thickening agent; (c) from about 10% to about 99% by weight of the composition, of an anhydrous liquid carrier; (d) from about 5 ppm to about 20% by weight of the composition, of a primary fragrance; and (e) from at least about 5 ppm by weight of the composition, of a secondary fragrance that is distinct from the primary fragrance and is included in a surfactant-free, water-releasable matrix, which renders the secondary fragrance within the matrix substantially odorless prior to aqueous activation, wherein the antiperspirant composition is substantially devoid of a malodor reducing agent.

DETAILED DESCRIPTION OF THE INVENTION

The antiperspirant compositions of the present invention may comprise, consist essentially of, or consist of, the essential components as well as optional ingredients described herein. As used herein, "consisting essentially of" means that the composition or component may include additional ingredients, but only if the additional ingredients do not materially alter the basic and novel characteristics of the claimed compositions or methods.

All percentages, parts and ratios are based upon the total weight of the topical compositions of the present invention and all measurements made are at 25° C., unless otherwise specified. All such weights as they pertain to listed ingredients are based on the active level and, therefore, do not include carriers or by-products that may be included in commercially available materials, unless otherwise specified.

The term "anhydrous" as used herein, unless otherwise specified, refers to those materials or compositions that are substantially free of added water. The term "anhydrous", however, as used herein can also mean that the composition contains water but that the water is isolated. The term "anhydrous" as used herein generally means that the material or composition preferably contains less than about 1%, less than about 0.5%, or zero percent, by weight of free or added water.

The term "particulate", as used herein, refers to compositions or materials that are comprised of solid particles and are not dissolved in water or other solvents.

As used herein, the term "cosmetically acceptable", as used herein, means that the product glides on smoothly during application, is non-irritating, and results in little or no visible residue (e.g. low residue performance) after application to the skin.

As used herein, the term "water-releasable" refers to the release of the secondary fragrance from the matrix upon aqueous activation so that its scent can be detected.

Antiperspirant Active

The antiperspirant compositions of the present invention may comprise a high-efficacy antiperspirant active. All high-efficacy antiperspirant actives within the present invention are suitable for application to human skin. The concentration of the high-efficacy antiperspirant active in the composition should be sufficient to provide the desired enhanced wetness protection that is perceivable by the user. For example, the active may be present in an amount of from at least about 0.1%, at least about 0.5%, or at least about 1% but no more than about 30%, no more than about 25% or no more than about 20%, by weight of the composition.

A. High Efficacy Antiperspirant Actives

As used herein, the term "high efficacy antiperspirant active" refers to any antiperspirant active that can provide enhanced wetness protection via conventional clinical measurement methods. Compositions of the present invention may include any compound, composition or other material having high efficacy antiperspirant activity wherein the active exhibits a metal to chloride ratio of from about 0.33 or from about 0.9 but no more than about 2.0, no more than about 1.5, no more than about 1.3, or no more than about 1.25. Such actives may include astringent metallic salts, especially inorganic and organic salts of aluminum, zirconium and zinc, as well as mixtures thereof. For example, suitable high efficacy antiperspirant actives may include zirconium-containing salts or materials, such as zirconyl oxyhalides, zirconyl hydroxyhalides, and mixtures thereof; and/or aluminum-containing or aluminum-only salts such as, for example, aluminum halides, aluminum chlorohydrate, aluminum hydroxyhalides, and mixtures thereof.

1. Aluminum Salts

Aluminum salts useful in the present invention include those that conform to the formula:

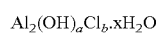

$Al_2(OH)_a Cl_b \cdot xH_2O$ wherein a is from about 0 to about 5; the sum of a and b is about 6; x is from about 1 to about 8; where a, b, and x may have non-integer values. For example, aluminum chlorohydroxides referred to as "¾ basic chlorohydroxide," wherein a is about 4.5; "⅚ basic chlorohydroxide", wherein a=5; and "⅔ basic chlorohydroxide", wherein a=4 may be used.

Processes for preparing aluminum salts are disclosed in U.S. Pat. No. 3,887,692, issued to Gilman on Jun. 3, 1975; U.S. Pat. No. 3,904,741, issued to Jones et al. on Sep. 9, 1975; and U.S. Pat. No. 4,359,456 issued to Gosling et al. on Nov. 16, 1982. A general description of these aluminum salts can also be found in *Antiperspirants and Deodorants*, Cosmetic Science and Technology Series Vol. 20, $2^{nd}$ edition, edited by Karl Laden. Mixtures of aluminum salts are described in British Patent Specification 1,347,950, filed in the name of Shin et al. and published Feb. 24, 1974.

2. Zirconium Salts

Zirconium salts for use in the present invention include those which conform to the formula:

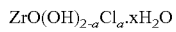

$$ZrO(OH)_{2-a}Cl_a \cdot xH_2O$$

wherein a is from about 0.5 to about 2; x is from about 1 to about 7; where a and x may both have non-integer values. These zirconium salts are described in Belgian Patent 825, 146, issued to Schmitz on Aug. 4, 1975. Useful to the present invention are zirconium salt complexes that additionally contain aluminum and glycine, commonly known as "ZAG complexes". These complexes contain aluminum chlorohydroxide and zirconyl hydroxy chloride conforming to the above-described formulas. Such ZAG complexes are described in U.S. Pat. No. 4,331,609, issued to Orr on May 25, 1982 and U.S. Pat. No. 4,120,948, issued to Shelton on Oct. 17, 1978.

3. Improved Aluminum-Only Salts

The present invention may also comprise an enhanced efficacy antiperspirant active which may further comprise an improved aluminum-only salt. Aluminum-only salts of the present invention may have an aluminum to anion ratio of, for example, about 1.1:1 to about 1.8:1, about 1.2 to about 1.6 or from about 1.4 to about 1.6. Such ratios are capable of providing the desired efficacy benefit while preventing manufacturing equipment corrosion that could occur at lower ratios. The aluminum-only salts of the present invention also have a polymer size distribution that includes at least about 20% Band III polymers. The aluminum-only salts of the present invention may also have, for example, a Band III polymer concentration of at least about 25% or at least about 30% when analyzed by Permeation Chromatography (GPC), which is a size exclusion chromatography method described hereinafter. The aluminum-only salts of the present invention also have a level of monomeric aluminum ranging, for example, at least from about 2%, at least from about 3%, or at least about 4% and no more than from about 20%, no more than from about 15% or no more than from about 12% of the total aluminum.

Gel Permeation Chromatography (GPC) Method

Aluminum-only salts of the present invention are dissolved in 0.01M nitric acid and chromatographed using 5 µl injections in a series of three consecutive Waters µ Porasil Columns, 3.9×300 mm, 10 µm packing. The mobile phase is a 0.01M nitric acid solution prepared by diluting 1.76 ml of 69-71% nitric acid to a volume of 2.0 L using deionized water. The flow rate is 0.8 ml $min^{-1}$ through the columns. The chromatographic system used is from Hewlett Packard and includes an 1100 series isocratic pump, autosampler, and an HP1047A refractive index detector (equivalent instrumentation can be used).

Samples are prepared by diluting 1 part of the powdered active to 100 parts total solution by weight with the 0.01M $HNO_3$ solution. This is done immediately prior to analysis to prevent degradation. Aqueous solutions of the aluminum hydroxyhalide salts used in the present invention may be diluted at 2 to 10 parts of aluminum hydroxyhalide salts to 100 parts total water depending upon concentration of the aluminum hydroxyhalide salts to provide a similar concentration to the powder samples.

Relative peak areas and area ratios are calculated using a Waters Millennium Data System (Version 2.10 or equivalent). The peaks observed in the chromatogram are designated in order of appearance on the chromatogram as Bands I, II, III and IV (see FIG. 1). The concentration of Band III polymers is determined by dividing the peak area of Band III by the sum of the peak area for Bands I, II, III, and IV.

Nuclear Magnetic Resonance (NMR) of Monomeric Aluminum

The aluminum-only salts of the present invention also have a level of monomeric aluminum ranging, for example, from at least about 2%, from at least about 3% or from at least about 4% to about 20%, to about 15% or to about 12% of the total aluminum, by weight of the composition. The concentration of monomeric aluminum level can be determined using the following method:

A set of $AlCl_3$ standards for 0 to about 2.5% aluminum chloride can be prepared by dissolving $AlCl_3 \cdot 6H_2O$ (JT Baker 0498-01 98.9% purity) in $D_2O$. The aluminum content in each (or in the original standard) can be determined by $EDTA/Zn^{2+}$ back titrations as described in the US Pharmacopeia 24.

NMR analysis of each standard can be performed using a Bruker Avance 400 MHz instrument (or equivalent) under quantitative conditions in which 32 scans can be signal averaged. Aluminum chloride can be used as the chemical shift reference material and assigned to 0.0 ppm. Resonance areas (at 0.0 ppm) for the standards are measured using the Avance X-win NMR v3.5 software package (or equivalent). A calibration plot of resonance area versus aluminum concentration (Al ppm) is then created. The slope (m) and intercept (b) of the calibration plot can then be determined using a linear least squares fit.

Samples of the aluminum-only salts of the present invention can be prepared by weighing out 10 parts of active ingredient and diluted to a total solution weight of 100 parts with $D_2O$ (Cambridge Isotope Labs DLM-4-100) with both sample weight and total solution weight being recorded. Solutions can be capped, shaken to solubilize and transferred into standard NMR tubes. Solutions can be analyzed using the same NMR method as the standard within 2 minutes of being prepared. The resonance area at 0.0 ppm of the sample can be determined and used to calculate the % monomeric aluminum via the following equation.

$$\% \text{ Monomeric Aluminum} = \frac{(\text{sample area} - \text{Intercept})}{\text{Slope}} \times (\text{sample solution weight}) \times \frac{(0.0001)}{(\text{sample weight} \times \% \text{ Al in sample})}$$

To use this equation, the percent aluminum in the sample must be determined. This may be accomplished using the $EDTA/Zn^{2+}$ back titrations as described in the US Pharmacopeia 24.

Enhanced efficacy antiperspirant actives using an improved aluminum-only salt may be processed as described in co-pending application, filed Jan. 13, 2005 as U.S. application Ser. No. 11/034,477 in the names of Swaile, et al.

Malodor Reducing Agent

The present invention may comprise a malodor reducing agent. Malodor reducing agents include components other than the antiperspirant active within the composition that act to eliminate the effect that body odor has on fragrance display. These agents may combine with the offensive body odor so that they are not detectable including, but not limited to, suppressing evaporation of malodor from the body, absorbing sweat or malodor, masking the malodor or microbiological activity on odor causing organisms. The concentration of the malodor reducing agent within the composition is sufficient to provide such chemical or biological means for reducing or eliminating body odor. Although the concentration will vary depending on the agent used, generally, the composition comprises from at least about 0.05%, from at least about 0.5%, or from at least about 1% to about 15%, to about 10% or to about 6%, by weight of the composition, of a malodor reducing agent.

Malodor reducing agents of the present invention may include, but are not limited to, pantothenic acid and its derivatives, petrolatum, menthyl acetate, uncomplexed cyclodextrins and derivatives thereof, talc, silica and mixtures thereof. Such agents may be used as described in U.S. Pat. No. 6,495,149, issued to Scavone, et al and US patent application 2003/0152539, filed Jan. 25, 2002 in the names of Scavone, et al.

For example, if panthenyl triacetate is used, the composition comprises from at least about 0.1% or from at least about 0.25% to about 3.0% or to about 2.0%, by weight of the composition, of the malodor reducing agent. Another example of a malodor reducing agent is petrolatum which may be included in an amount of from at least about 0.10% or from at least about 0.5% to about 15% or to about 10%, by weight of the composition. A combination may also be used as the malodor reducing agent including, but not limited to, panthenyl triacetate and petrolatum at levels of from at least about 0.1% or from at least about 0.5% to about 3.0% or to about 10%, by weight of the composition. Menthyl acetate, a derivative of menthol that does not have a cooling effect, may be included from at least about 0.05% or from at least about 0.01% to about 2.0% or to about 1.0%, by weight of the composition. The malodor reducing agent of the present invention may be in the form of a liquid or a semi-solid such that it does not contribute to product residue.

In accordance with one embodiment, compositions of the present invention are substantially devoid of a malodor reducing agent; that is, the composition contains less than 0.05%, by weight, of a malodor reducing agent.

Suspending/Thickening Agent

The antiperspirant compositions of the present invention also comprise thickening agents to help provide the composition with the desired viscosity, rheology, texture and/or product hardness, or to otherwise help suspend any dispersed solids or liquids within the composition. The term "thickening agent" may include any material known or otherwise effective in providing suspending, gelling, viscosifying, solidifying or thickening properties to the composition or which otherwise provide structure to the final product form. These thickening agents may include gelling agents, polymeric or nonpolymeric agents, inorganic thickening agents, or viscosifying agents. The thickening agents may include organic solids, silicone solids, crystalline or other gellants, inorganic particulates such as clays or silicas, or combinations thereof.

The concentration and type of the thickening agent selected for use in the antiperspirant composition of the present invention will vary depending upon the desired product form, viscosity, and hardness. The thickening agents suitable for use herein, may have a concentration range of from at least about 0.1%, at least about 3%, or at least about 5% to about 35%, to about 20%, or to about 10%, by weight of the composition.

Non-limiting examples of suitable gelling agents of the present invention include fatty acid gellants, salts of fatty acids, hydroxyl acids, hydroxyl acid gellants, esters and amides of fatty acid or hydroxyl fatty acid gellants, cholesterolic materials, dibenzylidene alditols, lanolinolic materials, fatty alcohols, triglycerides, sucrose esters such as SEFA behenate, inorganic materials such as clays or silicas, other amide or polyamide gellants, and mixtures thereof. Concentrations of all such gelling agents may be from at least about 0.1%, at least about 1%, or at least about 5% and no more than about 25%, no more than about 15%, or no more than about 10%, by weight of the composition.

Suitable gelling agents include fatty acid gellants such as fatty acid and hydroxyl or alpha hydroxyl fatty acids, having from about 10 to about 40 carbon atoms, and ester and amides of such gelling agents. Non-limiting examples of such gelling agents include, but are not limited to, 12-hydroxystearic acid, 12-hydroxylauric acid, 16-hydroxyhexadecanoic acid, behenic acid, eurcic acid, stearic acid, caprylic acid, lauric acid, isostearic acid, and combinations thereof. Preferred gelling agents are 12-hydroxystearic acid, esters of 12-hydroxystearic acid, amides of 12-hydroxystearic acid and combinations thereof.

Other suitable gelling agents include amide gellants such as disubstituted or branched monoamide gellants, monsubstituted or branched diamide gellants, triamide gellants, and combinations thereof, including n-acyl amino acid derivatives such as n-acyl amino acid amides, n-acyl amino acid esters prepared from glutamic acid, lysine, glutamine, aspartic acid, and combinations thereof. Other suitable amide gelling agents are described in U.S. Pat. No. 5,429,816, issued Jul. 4, 1995, and U.S. Pat. No. 5,840,287, filed Dec. 20, 1996.

Still other examples of suitable gelling agents include fatty alcohols having at least about 8 carbon atoms, at least about 12 carbon atoms but no more than about 40 carbon atoms, no more than about 30 carbon atoms, or no more than about 18 carbon atoms. For example, fatty alcohols include but are not limited to cetyl alcohol, myristyl alcohol, stearyl alcohol and combinations thereof.

Non-limiting examples of suitable tryiglyceride gellants include tristearin, hydrogenated vegetable oil, trihydroxysterin (Thixcin® R, available from Rheox, Inc.), rape seed oil, castor wax, fish oils, tripalmitin, Syncrowax® HRC and Syncrowax® HGL-C (Syncrowax® available from Croda, Inc.).

Other suitable thickening agents include waxes or wax-like materials having a melt point of above 65° C., more typically from about 65° C. to about 130° C., examples of which include, but are not limited to, waxes such as beeswax, carnauba, bayberry, candelilla, montan, ozokerite, ceresin, hydrogenated castor oil (castor wax), synthetic waxes and microcrystalline waxes. Castor wax is preferred. Other high melting point waxes are described in U.S. Pat. No. 4,049,792, Elsnau, issued Sep. 20, 1977.

Further thickening agents for use in the antiperspirant compositions of the present invention may include inorganic particulate thickening agents such as clays and colloidal pyrogenic silica pigments. For example, colloidal pyrogenic silica pigments such as Cab-O-Sil®, a submicroscopic particulated pyrogenic silica may be used. Other known or otherwise effective inorganic particulate thickening agents that are commonly used in the art can also be used in the antiperspirant compositions of the present invention. Concentrations of particulate thickening agents may range, for example, from at least about 0.1%, at least about 1%, at least about 5% but no more than about 35%, no more than about 15%, no more than about 10% or no more than about 8%, by weight of the composition.

Suitable clay thickening agents include montmorillonite clays, examples of which include bentonites, hectorites, and colloidal magnesium aluminum silicates. These and other suitable clays may be hydrophobically treated, and when so treated will generally be used in combination with a clay activator. Non-limiting examples of suitable clay activators include propylene carbonate, ethanol, and combinations thereof. When clay activators are present, the amount of clay activator will typically range from at least about 40%, at least about 25%, at least about 15% but no more than about 75%, no more than about 60%, or no more than about 50%, by weight of the clay.

Hardness

The antiperspirant compositions of the present invention may have a product hardness of from at least about 600 gram·force, from about 750 gram·force, or from about 800 gram·force but no more than about 5,000 gram·force, from about 2,000 gram·force, or from about 1,400 gram·force.

The term "product hardness" or "hardness" as used herein is a reflection of how much force is required to move a penetration cone a specified distance and at a controlled rate into a solid antiperspirant composition under the following test conditions. Higher values represent harder product, and lower values represent softer product. These values are measured at 27° C., 15% relative humidity, using a TA-XT2 Texture Analyzer, available from Texture Technology Corp., Scarsdale, New York, U.S.A. The product hardness value as used herein represents the peak force required to move a standard 45° angle penetration cone through the composition for a distance of 10 mm at a rate of 2 mm/second. The standard cone is available from Texture Technology Corp., as part number TA-15, and has a total cone length of about 24.7 mm, angled cone length of about 18.3 mm, a maximum diameter of the angled surface of the cone of about 15.5 mm. The cone is a smooth, stainless steel construction and weighs about 17.8 grams.

The product hardness may be selected for each antiperspirant composition to help provide the desired application rheology, thus resulting in the desired low-residue application layer as applied to the skin. Although low-residue performance can be controlled by a variety of mechanisms known in the antiperspirant art, the compositions of the present invention may exhibit low-residue performance, at least in part, by controlling product hardness.

Anhydrous Liquid Carrier

The antiperspirant compositions of the present invention may comprise anhydrous liquid carriers at concentrations ranging from at least about 10%, at least about 15%, at least about 20%, at least about 25% but no more than about 99%, no more than about 70%, no more than about 60% or no more than about 50%, by weight of the composition. Such concentrations will vary depending upon variables such as product form, desired product hardness, and selection of other ingredients in the composition. The anhydrous carrier may be any anhydrous carrier known for use in personal care applications or otherwise suitable for topical application to the skin. For example, anhydrous carriers of the present invention may include, but are not limited to volatile and nonvolatile fluids.

A. Volatile Fluid

The antiperspirant composition of the present invention may further comprise a volatile fluid such as a volatile silicone carrier whose concentration may be from about 20% or from about 30% but no more than about 80% or no more than about 60%, by weight of the composition. The volatile silicone of the solvent may be cyclic, linear, and/or branched chain silicone. "Volatile silicone", as used herein, refers to those silicone materials that have measurable vapor pressure under ambient conditions. Non-limiting examples of suitable volatile silicones are described in Todd et al., "Volatile Silicone Fluids for Cosmetics", Cosmetics and Toiletries, 91:27-32 (1976).

The volatile silicone may be a cyclic silicone having from at least about 3 silicone atoms or from at least about 5 silicone atoms but no more than about 7 silicone atoms or no more than about 6 silicone atoms. For example, volatile silicones may be used which conforms to the formula:

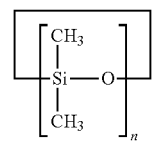

wherein n is from about 3 or from about 5 but no more than about 7 or no more than about 6. These volatile cyclic silicones generally have a viscosity of less than about 10 centistokes at 25° C. Suitable volatile silicones for use herein include, but are not limited to, Cyclomethicone D5 (commercially available from G. E. Silicones); Dow Corning 344, and Dow Corning 345 (commercially available from Dow Corning Corp.); and GE 7207, GE 7158 and Silicone Fluids SF-1202 and SF-1173 (available from General Electric Co.). SWS-03314, SWS-03400, F-222, F-223, F-250, F-251 (available from SWS Silicones Corp.); Volatile Silicones 7158, 7207, 7349 (available from Union Carbide); Masil. SF-V (available from Mazer) and combinations thereof. If the antiperspirant composition of the present invention is contained within an aerosol product, any volatile hydrocarbon or propellant commonly used in the art may be used as the carrier.

B. Non-Volatile Fluid

The antiperspirant composition of the present invention may further comprise a non-volatile fluid. These non-volatile fluids may be either non-volatile organic fluids or non-volatile silicone fluids.

1. Non-Volatile Organic Fluids

The antiperspirant composition of the present invention may further comprise non-volatile organic fluids. The non-volatile organic fluid can be present at concentrations ranging from about 1%, from about 2% but no more than about 20% or no more than about 15%, by weight of the composition.

Non-limiting examples of nonvolatile organic fluids include, but are not limited to, mineral oil, PPG-14 butyl ether, isopropyl myristate, petrolatum, butyl stearate, cetyl octanoate, butyl myristate, myristyl myristate, C12-15 alkylbenzoate (e.g., Finsolv.™), dipropylene glycol dibenzoate, PPG-15 stearyl ether benzoate and blends thereof (e.g. Finsolv TPP), neopentyl glycol diheptanoate (e.g. Lexfeel 7 supplied by Inolex), octyldodecanol, isostearyl isostearate, octododecyl benzoate, isostearyl lactate, isostearyl palmitate, isononyl/isononoate, isoeicosane, octyldodecyl neopentanate, hydrogenated polyisobutane, and isobutyl stearate. Many such other carrier liquids are disclosed in U.S. Pat. No. 6,013,248 (Luebbe et al.) and U.S. Pat. No. 5,968,489 (Swaile et al).

2. Nonvolatile Silicone Fluids

The antiperspirant compositions of the present invention may further comprise a non-volatile silicone fluid. The non-volatile silicone fluid may be a liquid at or below human skin temperature, or otherwise in liquid form within the anhydrous antiperspirant composition during or shortly after topical application: The concentration of the non-volatile silicone may be from about 1%, from about 2% but no more than about 15% or no more than about 10%, by weight of the composition. Nonvolatile silicone fluids of the present invention may include those which conform to the formula:

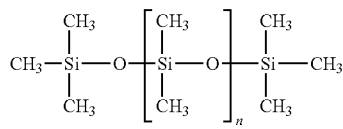

wherein n is greater than or equal to 1. These linear silicone materials may generally have viscosity values of from about 5 centistokes, from about 10 centistokes but no more than about 100,000 centistokes, no more than about 500 centistokes, no more than about 200 centistokes or no more than about 50 centistokes, as measured under ambient conditions.

Specific non limiting examples of suitable nonvolatile silicone fluids include Dow Corning 200, hexamethyldisiloxane, Dow Corning 225, Dow Corning 1732, Dow Corning 5732, Dow Corning 5750 (available from Dow Corning Corp.); and SF-96, SF-1066 and SF 18(350) Silicone Fluids (available from G.E. Silicones).

Low surface tension non-volatile solvent may be also be used. Such solvents may be selected from the group consisting of dimethicones, dimethicone copolyols, phenyl trimethicones, alkyl dimethicones, alkyl methicones, and mixtures thereof. Low surface tension non-volatile solvents are also described in U.S. Pat. No. 6,835,373 (Kolodzik et al.).

Primary Fragrance

Antiperspirant compositions of the present invention may further comprise a primary fragrance to help cover or mask malodors resulting from perspiration, or which otherwise provide the compositions with the desired perfume or unscented/neutral aroma. The scented primary fragrance may include any perfume or perfume chemical suitable for topical application to the skin and suitable for use in antiperspirant compositions.

The concentration of the primary fragrance in the antiperspirant compositions should be effective to provide the desired aroma including, but not limited to, unscented. As used herein, "unscented" refers to the level of fragrance wherein the level of fragrance is below 5 ppm such that the fragrance is absent or undetected. Generally, the concentration of the scented primary fragrance is from at least about 5 ppm, from about 0.1%, from about 0.5% but no more than about 20%, no more than about 10%, no more than about 5%, or no more than about 2%, by weight of the composition. The primary fragrance should not impart excessive stinging to the skin, especially broken or irritated skin, at the concentrations disclosed herein. The primary fragrance may be included in the antiperspirant compositions of the present invention as a free perfume.

Secondary Fragrance

The secondary fragrance of the present invention should be substantially different and distinct from the composition of the primary fragrance in order to overcome the effect of fragrance habituation and to make the second fragrance noticeable over the primary fragrance. Generally, antiperspirant compositions of the present invention may comprise from about 5 ppm, from about 0.1%, from about 0.5% but no more than about 20%, no more than about 10%, no more than about 5%, or no more than about 2%, by weight of the composition. The secondary fragrance should not impart excessive stinging to the skin, especially broken or irritated skin, at the concentrations disclosed herein.

Any perfume or perfume chemical suitable for topical application to the skin and suitable for use in antiperspirant compositions may be used as the secondary fragrance, however, it will not be included within the composition as a free perfume. The secondary fragrance will be included in a surfactant-free, water-releasable matrix, which renders the secondary fragrance within the matrix initially substantially odorless. The secondary fragrance may be selected from the group consisting of perfumes, highly volatile perfume materials having a boiling point of less than about 250° C., High Impact Accord perfume materials, and mixtures thereof. Such fragrances will be included within a matrix selected such as cyclodextrin complexes as described herein.

Perfumes

High Impact Accord (HIA) Perfumes

HIA perfume ingredients are characterized by their respective boiling point (B.P.), octanol/water partition coefficient (P) and odor detection threshold ("ODT"). The "octanol/water partition coefficient (P)" of a perfume ingredient is the ratio between its equilibrium concentrations in octanol and in water. The boiling points of many perfume ingredients, at standard pressure (760 mm Hg) are given in, e.g., "Perfume and Flavor Chemicals (Aroma Chemicals)," Steffen Arctander, published by the author.

The logP values of many perfume ingredients have been reported; for example, the Pomona92 database, available from Daylight Chemical Information Systems, Inc. (Daylight CIS), Irvine, Calif., contains many, along with citations to the original literature. However, the logP values are most conveniently calculated by the "CLOGP" program, also available from Daylight CIS. This program also lists experimental logP values when they are available in the Pomona92 database. The "calculated logP" (ClogP) is determined by the fragment approach of Hansch and Leo (cf., A. Leo, in Comprehensive Medicinal Chemistry, Vol. 4, C. Hansch, P. G. Sammens, J. B. Taylor and C. A. Ramsden, Eds., p. 295, Pergamon Press, 1990). The fragment approach is based on the chemical structure of each perfume ingredient, and takes into account the numbers and types of atoms, the atom connectivity, and chemical bonding. The ClogP values, which are the most reliable and widely used estimates for this physicochemical property, are preferably used instead of the experimental logP values in the selection of perfume ingredients which are useful in the present invention. Odor detection thresholds are determined using a gas chromotograph as disclosed in co-pending application, Browne, et al., filed Jun. 9, 2004.

For the first class of perfume ingredients, each Class 1 HIA perfume ingredient of this invention may have a B.P., determined at the normal, standard pressure of 760 mm Hg, of 275° C. or lower and an ODT of less than or equal to 50 parts per billion (ppb). Since the partition coefficients of the perfume ingredients of this invention may have high values, they are more conveniently given in the form of their logarithm to the base 10 logP. The perfume ingredients of this invention have a ClogP of 2 and higher.

Table 1 gives some non-limiting examples of HIA perfume ingredients of Class 1.

TABLE 1

HIA Perfume Ingredients of Class 1

HIA Ingredients of Class 1

Ionone beta
4-(2,2,6-Trimethylcyclohex-1-enyl)-2-but-en-4-one
2,4-Decadienoic acid, ethyl ester (E,Z)-
6-(and -8) isopropylquinoline
Acetaldehyde phenylethyl propyl acetal
Acetic acid, (2-methylbutoxy)-, 2-propenyl ester
Acetic acid, (3-methylbutoxy)-, 2-propenyl ester
Benzaldehyde
2,6,10-Trimethyl-9-undecenal
Glycolic acid, 2-pentyloxy-, allyl ester
Hexanoic acid, 2-propenyl ester
1-Octen-3-ol
trans-Anethole
iso butyl (z)-2-methyl-2-butenoate
Anisaldehyde diethyl acetal
Benzenepropanal, 4-(1,1-dimethylethyl)
2,6-Nonadien-1-ol
3-methyl-5-propyl-cyclohexen-1-one
Buranoic acid, 2-methyl-, 3-hexenyl ester, (Z)-
Acetaldehyde, [(3,7-dimethyl-6-octenyl)oxy]-
Lauronitrile
2,4-dimethyl-3-cyclohexene-1-carbaldehyde
2-Buten-1-one, 1-(2,6,6-trimethyl-1,3-cyclohexadien-1-yl)-
2-Buten-1-one, 1-(2,6,6-trimethyl-2-cyclohexen-1-yl)-, (E)-
Ethyl-2-Methyl Butyrate
gamma-Decalactone
trans-4-decenal
decanal
2-Pentylcyclopentanone
1-(2,6,6, Trimethyl 3 Cyclohexen-1-yl)-2 Buten-1-one)
2,6-dimethylheptan-2-ol
Benzene, 1,1 '-oxybis-
4-Penten-1-one, 1-(5,5-dimethyl-1-cyclohexen-1-yl)-
Butanoic acid, 2-methyl-, ethyl ester
Ethyl anthranilate
2-Oxabicyclo [2.2.2]octane, 1,3,3-trimethyl-
2-6-nonadienal
Eugenol
Citralva Plus
Damarose Alpha
3-(3-isopropylphenyl)butanal
methyl 2-octynoate
Decyl Aldehyde
Methyl-2-nonenoate
4-(2,6,6-trimethyl-1-cyclohexen-1-yl)-3-buten-2-one
Pyrazine, 2-methoxy-3-(2-methylpropyl)-
Quinoline, 6-secondary buty
Isoeugenol
Mandarin Aldehyde
Oxane
2H-Pyran-2-one, tetrahydro-6-(3-pentenyl)-
Cis-3-Hexenyl Methyl Carbonate
Linalool
1,6,10-Dodecatriene, 7,11-dimethyl-3-methylebe-, (E)-
2,6-dimethyl-5-heptenal
4,7 Methanoindan 1-carboxaldehyde, hexahydro
2-methylundecanal
Methyl 2-nonynonate
1,1-dimethoxy-2,2,5-trimethyl-4-hexene
melonal
Methyl Nonyl Acetaldehyde
Undecalactone
Trans-2-Hexanal
Pino Acetaldehyde
Neobutenone
Benzoic acid, 2-hydroxy-, methyl ester
4-Penten-1-one, 1-(5,5-dimethyl-1-cyclohexen-1-yl)
2H-Pyran, 3,6-dihydro-4 methyl-2-(2-methyl-1-propenyl)-
2,6-Octadienenitrile, 3,7-dimethyl-, (Z)-
2,6-nonadienal
6-Nonenal, (Z)-
nonanal
octanal
2-Nonenenitrile
Acetic acid, 4-methylphenyl ester
Gamma Undecalactone

TABLE 1-continued

HIA Perfume Ingredients of Class 1

HIA Ingredients of Class 1

2-norpinene-2-propionaldehyde 6,6 dimethyl
4-nonanolide
9-decen-1-ol
2H-Pyran, tetrahydro-4-methyl-2-(2-methyl-1-propenyl)-
5-methyl-3-heptanone oxime
Octanal, 3,7-dimethyl-
4-methyl-3-decen-5-ol
10-Undecen-1-al
Pyridine, 2-(1-theylpropyl)-
Spiro [furan-2(3H), 5'[4,7]methanol[5H]indene], decahydro-
Anisic Aldehyde
Flor Acetate
Rose Oxide
Cis 3 Hexenyl Salicylate
Methyl Octin Carbonate
Ethyl-2-Methyl Butyrate The secondary fragrance of the invention may also comprisee one or more HIA perfume ingredients of Class 1.

Class 1 HIA perfume ingredients are very effusive and very noticeable when included in a composition. Of the perfume ingredients in a given perfume composition, from at least about 15% to about 75% or to about 50%, by weight of the composition, are Class 1 HIA perfume ingredients.

The secondary fragrance of the invention may also comprisee one or more HIA perfume ingredients of Class 2.

Class 2 HIA perfume ingredients leave a lingering scent on the skin. Of the perfume ingredients in a given perfume composition, from at least about 0.01% to about 30% or to about 25%, by weight of the composition, are Class 2 HIA perfume ingredients.

For the second class of perfume ingredients, each Class 2 HIA perfume ingredient of this invention has a B.P., determined at the normal, standard pressure of about 760 mm Hg, of greater than 275° C. and an ODT of less than or equal to 50 parts per billion (ppb). Since the partition coefficients of the perfume ingredients of this invention have high values, they are more conveniently given in the form of their logarithm to the base 10 logP. The perfume ingredients of this invention have a ClogP of at least about 4.

Table 2 gives some non-limiting examples of HIA perfume ingredients of Class 2.

TABLE 2

HIA Perfume Ingredients of Class 2

Naphthol(2,1-B)-furan,3A-Ethyl Dodecahydro-6,6,9A-Trimethyl
Natural Sinensal
Para Hydroxy phenyl Butanone
2-(Cyclododecyl)-propan-1-ol
Oxacycloheptadecan-2-one
Ketone,Methyl-2,6,10-Trimethyl-2,5,9-Cyclododecatriene-1-yl
8alpha,12oxido-13,14,15,16-tetranorlabdane
Cyclohexane Propanol 2,2,6 Trimethyl-Alpha,Propyl
6,7-Dihydro-1,1,2,3,3-Pentamethyl-4(5H)-Indanone
8-Cyclohexadecan-1-one
2-(2-(4Methyl-3-cyclohexan-1-yl)-cyclopentanone
Oxacyclohexadecen-2-one
3-Methyl-4(5)-Cyclopentadecenone
3-Methyl-5-(2,2,3-trimethyl-3-cyclopenten-1-yl)-4-penten-2-ol
2,4,-Dimethyl-2-(1,1,44,-tetramethyl)tetralin-6-yl)- 1,3-dioxolane
Tridecene-2-nitrile
7,Acetyl,1,2,3,4,5,6,7,8-Octahydro-1,1,6,7-Tetra Methyl Naphthalene
5-Cyclohexadecenone-1

Secondary fragrance compositions of the present invention may also comprise optional conventional perfume composition materials such as other perfume ingredients not falling within either Class 1 or Class 2, odorless solvents or oxidation inhibitors, or mixtures thereof. Secondary fragrance compositions of the present invention may comprise up to 75%, by weight of the composition, of Class 1 and Class 2 HIA perfumes.

Highly Volatile Perfumes

The secondary fragrance of the present invention may be a highly volatile perfume. It is believed that highly volatile perfume materials can provide fragrance aesthetics such as fresh and clean odor impressions.

Nonlimiting examples of highly volatile perfume materials that have a boiling point less than or equal to 250° C. include, but are not limited to, anethole, benzaldehyde, decyl aldehyde, benzyl acetate, benzyl alcohol, benzyl formate, benzyl propionate, iso-bornyl acetate, camphene, cis-citral (neral), citronellal, citronellol, citronellyl acetate, paracymene, decanal, dihydrolinalool, dihydromyrcenol, methyl benzyl carbinyl acetate, dimethyl benzyl carbinyl acetate, dimethyl phenyl carbinol, eucalyptol, helional, geranial, geraniol, geranyl acetate, geranyl nitrile, cis-3-hexenyl acetate, dihydrocitronellal, d-limonene, linalool, linalool oxide, tetra-hydro linalool, alpha-methyl ionone, methyl nonyl acetaldehyde, methyl phenyl carbinyl acetate, laevo-menthyl acetate, menthone, iso-menthone, myrcene, myrcenyl acetate, myrcenol, nerol, neryl acetate, nonyl acetate, phenyl ethyl alcohol, phenyl acetaldehyde, alpha-pinene, beta-pinene, gamma-terpinene, terpineol, alpha-terpineol, beta-terpineol, terpinyl acetate, vertenex (para-tertiary-butyl cyclohexyl acetate), gamma-methyl ionone, undecalactone, undecylenic aldehyde, alpha-damascone, beta-damascone, amyl acetate, lemon oil, orange oil, and mixtures thereof.

Matrix

Cyclodextrin Complex

The antiperspirant compositions of the present invention may include a secondary fragrance that complexes with a cyclodextrin. As used herein, the term "cyclodextrin" includes any of the known cyclodextrins such as unsubstituted cyclodextrins containing from about six to about twelve glucose units, especially alpha-cyclodextrin, beta-cyclodextrin, gamma-cyclodextrin and/or their derivatives and/or mixtures thereof. For example, the present invention may use cyclodextrins selected from the group consisting of beta-cyclodextrin, hydroxypropyl alpha-cyclodextrin, hydroxypropyl beta-cyclodextrin, methylated-alpha-cyclodextrin, methylated-beta-cyclodextrin, and mixtures thereof.

Cyclodextrins and/or mixtures thereof are useful to the present invention since they are particularly known to absorb body odors. Therefore, an added benefit of using cyclodextrins as complexing aids for the secondary fragrance is that once the matrix solubilizes and the fragrance is released, the cyclodextrin may then become available to absorb malodor. Cyclodextrins may be included within the matrix of the present invention from at least about 0.1%, from at least about 1%, from at least about 2%, or from at least about 3% to about 25%, to about 20%, to about 15% or to about 10%, by weight of the composition.

The release of the secondary fragrance from the complex between cyclodextrin and the secondary fragrance occurs rapidly when wetted with body fluids. This is convenient for use within the present invention since the secondary fragrance should initially remain odorless until aqueous activation and solubilization of the matrix. For example, cyclodextrins having a small particle size may complex with the secondary fragrance of the present invention and remain odorless within the composition until the body perspires. Particularly, β-Cyclodextrins may be used in the present invention since they have a high tolerance to dissolve in water and will release the fragrance more slowly. Cyclodextrins having a small particle size may aid in providing higher cyclodextrin surface availability for activation. As used herein, the particle size refers to the largest dimension of the particle. Small particle cyclodextrins useful in the present invention may have a particle of less than about 50 microns, less than about 25 microns, or less than about 10 microns. A more complete description of the cyclodextrins, cyclodextrin derivatives and cyclodextrin particle sizes useful in the matrices of the present invention may be found in U.S. Pat. No. 5,429,628, issued to Trinh et al. on Jul. 4, 1995.

Optional Materials

The antiperspirant compositions of the present invention may further comprise additional optional materials known for use in antiperspirant, deodorant or other personal care products, including those materials that are known to be suitable for topical application to skin. Non limiting examples include dyes or colorants, emulsifiers, distributing agents, pharmaceuticals or other topical actives, skin conditioning agents or actives, deodorant agents, antimicrobials, preservatives, surfactants, processing aides such as viscosity modifiers and wash-off aids. Examples of such optional materials are described in U.S. Pat. No. 4,049,792 (Elsnau); U.S. Pat. No. 5,019,375 (Ianner et al.) and U.S. Pat. No. 5,429,816 (Hofrichter et al.).

Product Form

The antiperspirant compositions of the present invention can be formulated as any known or otherwise effective product form for providing topical application of antiperspirant or deodorant active to the desired area of the skin. Non-limiting examples of such product forms include liquids (e.g., aerosols, pump sprays, roll-ons), solids (e.g., gel solids, invisible solids, wax solid sticks), semi-solids (e.g., creams, soft solids, lotions), and the like. For example, the antiperspirant compositions of the present invention may be semi-solids or solids.

The antiperspirant products are generally stored in and dispensed from a suitable package or applicator device, such as a cream dispenser with perforated application domes, etc. These packages should be sufficiently closed to prevent excessive loss of volatiles prior to application.

Method of Manufacture

The antiperspirant compositions of the present invention may be prepared by any known or otherwise effective technique, suitable for providing an anhydrous composition of the desired form and having the essential materials described herein. Many such techniques are described in the antiperspirant/deodorant formulation arts for the described product forms.

The product of the present invention may be manufactured by limiting the length of time that the secondary fragrance within the water soluble matrix is exposed to heat to prevent deterioration of the inclusion agent. This can be achieved by addition of the secondary fragrance within the water soluble matrix just prior to cooling the antiperspirant composition to room temperature. Another suitable method of manufacture is described in co-pending application filed by Walling et al. on Mar. 1, 2005, entitled "Direct Contact Quench Crystallization Process and Cosmetic Product Produced Thereby".

Method of Use

The antiperspirant compositions of the present invention may be applied topically to the underarm or other suitable area of the skin in an amount effective to reduce or inhibit perspiration wetness. Compositions of the present invention may be applied in an amount ranging from at least about 0.1 gram to about 20 grams, to about 10 grams, or to about 1 gram. The composition may be applied to the underarm at least about one or two times daily, preferably once daily, to achieve effective antiperspirant reduction or inhibition over an extended period.

The antiperspirant composition can also be applied every other day, or every third or fourth day, and then optionally to supplement application on off-days with other personal care products such as deodorants and/or conventional antiperspirant formulations.

Compositions of the present invention may be applied to skin, wherein the volatile anhydrous carrier leaves behind a skin-adhering polymer and active-containing film. This film is positioned over the sweat ducts and resists flaking and/or rub-off, thereby being present through multiple perspiration episodes.

EXAMPLES

The following Examples can be made in accordance with the present invention.

An example of a high impact accord is given below in Example 1. An example of an Invisible Solid Antiperspirant is given below in Example 2. The high impact accord in Example 2 is complexed with beta cyclodextrin at 8.50% by weight of the inclusion complex. The High Impact Accord of Example 1 is processed according to co-pending application U.S. 60/682,600 filed by Deckner, et al. on May 19, 2005, entitled "Oil Encapsulation".

Example 1

| HIA Perfume Ingredient name | Conc (% w/w) | ODT. (ppb) | Boling Point (° C.) | ClogP |
|---|---|---|---|---|
| 2-6-nonadienal | 0.5 | ≤50 | 210 | 2.7 |
| Adoxal | 0.5 | ≥50 | 276 | 5.2 |
| Allyl Heptanoate | 5.5 | ≥50 | 212 | 3.4 |
| Beta Gamma Hexenol | 1.0 | ≥50 | 159 | 1.4 |
| Cis 3 Hexenyl Acetate | 2.25 | ≥50 | 179 | 2.3 |
| Citralva Plus | 1.0 | ≤50 | 249 | 3.3 |
| d-limonene | 11.3 | ≥50 | 170 | 4.4 |
| Damarose Alpha | 0.5 | ≤50 | 257 | 3.6 |
| Decyl Aldehyde | 2.25 | ≤50 | 218 | 4.0 |
| Hexyl Cinnamic Aldehyde | 9.0 | ≥50 | 334 | 4.9 |
| Mandarin Aldehyde | 3.5 | ≤50 | 261 | 4.6 |
| ethyl-2-methyl butyrate | 3.5 | ≤50 | 132 | 2.1 |
| Melonal | 1.2 | ≤50 | 188 | 2.6 |
| Methyl Nonyl Acetaldehyde | 1.0 | ≤50 | 237 | 4.9 |
| Natural Sinensal | 3.5 | ≤50 | 295 | 4.5 |
| Nectaryl | 9.0 | ≥50 | 317 | 4.4 |
| Neobutenone | 0.5 | ≤50 | 233 | 3.63 |
| decyl aldehyde | 9.0 | ≤50 | 218 | 4 |
| Para Hydroxy Phenyl Butanone | 1.5 | ≤50 | 301 | 1.1 |
| Pino Acetaldehyde | 3.5 | ≤50 | 257 | 3.3 |
| Trans-2 Hexenal | 0.5 | ≤50 | 145 | 1.6 |
| Undecalactone | 9.0 | ≥50 | 260 | 3.8 |
| methyl-2-nonenoate | 3.5 | ≤50 | 211 | 3.97 |
| Verdox | 11.5 | ≥50 | 237 | 4.1 |
| Ionone Beta | 5.5 | ≤50 | 276 | 3.8 |

The antiperspirants are prepared in the lab using conventional preparation procedures, according to one skilled in the art of making antiperspirants.

Examples 2-6

| | II | III | IV | V | VI |
|---|---|---|---|---|---|
| | Invisible Solid Antiperspirant Sticks [Conc (% w/w)] | | | Cream Antiperspirant Sticks [Conc (% w/w)] | |
| Aluminum Zirconium Tetrachlorohydrate glycine[a] | 25.25 | 25.25 | 25.25 | 25.25 | 25.25 |
| Cyclopentasiloxane | QS | QS | QS | QS | QS |
| Dimethicone (10 Cst) | | | | 5.00 | 5.00 |
| Petrolatum | 5.00 | 4.70 | 4.70 | 5.00 | 5.00 |
| Ozokerite | 9.00 | 1.00 | 1.00 | | |
| Stearyl Alcohol | | 12.00 | 12.00 | | |
| Syncrowax HGLC | | | | 1.25 | 1.25 |
| Fully Hydrogenated High Erucic Acid Rapeseed Oil | | | | 5.00 | 5.00 |
| Synrowax ERL-C | 4.00 | | | | |
| PPG-14 Butyl Ether | 9.00 | 9.00 | 9.00 | | |
| Castor Wax | | 3.50 | 3.50 | | |
| Fumed Silica | | | | 1.00 | |
| Mineral Oil | | 0.50 | 0.50 | | |
| Talc | | 4.00 | 4.00 | | |
| Behenyl Alcohol | | 0.20 | 0.20 | | |
| d-Panthenyl Triaceate | | 1.00 | 1.00 | | |
| Primary Fragrance | 1.25 | 0.00 | 1.25 | 0.75 | 0.75 |
| Secondary Fragrance | 2.81 | 2.80 | 1.80 | 0.50 | 3.50 |
| High Impact Accord (from Ex.1) In Beta Cyclodextrin complex | | | | | |

[a]Metal to Chloride metal ratio = 1.25; 75% anhydrous unbuffered active level (Westwood Chemical Co.)

All documents cited in the Detailed Description of the Invention are, in relevant part, incorporated herein by reference; the citation of any document is not to be construed as an admission that it is prior art with respect to the present invention. To the extent that any meaning or definition of a term in this document conflicts with any meaning or definition of the term in a document incorporated herein by reference, the meaning or definition assigned to the term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An anhydrous antiperspirant composition comprising:
   a. from about 0.1% to about 30% by weight of the composition, of a high-efficacy antiperspirant active selected from the group consisting of aluminum halides, aluminum chlorohydrates, aluminum hydroxyhalides, zirconyl oxyhalides, zirconyl hyroxyhalides, aluminum-only salts, and mixtures thereof;
   b. from about 0.1% to about 35% by weight of the composition, of a thickening agent;
   c. from about 10% to about 99% by weight of the composition, of an anhydrous liquid carrier;
   d. from about 0.1% to about 5%, by weight of the composition, of a primary fragrance; and e. from about 0.1% to about 5% by weight of the composition, of a secondary fragrance that is distinct from the primary fragrance and is included in a surfactant-free, water-releasable matrix, the secondary fragrance comprises perfume chemicals that are not included in the primary fragrance, wherein:

the surfactant-free, water-releasable matrix comprises a beta-cyclodextrin complex;

the anhydrous antiperspirant composition is a solid having a product hardness value of from 600 gram·force to 5000 gram·force; and the antiperspirant composition is devoid of a malodor reducing agent other than the high-efficacy antiperspirant active.

2. The anhydrous antiperspirant composition of claim 1, wherein the antiperspirant active is an aluminum-only salt having a Band III polymer concentration of at least about 20%, an aluminum to anion ratio of from about 1.1:1 to about 1.8:1 and a level of monomeric aluminum of from about 2% to about 20% of the total aluminum.

3. The anhydrous antiperspirant composition of claim 1, wherein the thickening agent is selected from the group consisting of organic solids, silicone solids, gellants, inorganic particulates, and mixtures thereof.

4. The anhydrous antiperspirant composition of claim 1, wherein the anhydrous liquid carrier is selected from the group consisting of volatile fluids, nonvolatile fluids, and mixtures thereof.

5. The anhydrous antiperspirant composition of claim 4, wherein the anhydrous liquid carrier is a volatile fluid and said volatile fluid is a volatile silicone.

6. The anhydrous antiperspirant composition of claim 1, wherein the secondary fragrance is selected from the group consisting of perfumes, highly volatile perfume materials having a boiling point of less than 250° C., High Impact Accord perfume materials, and mixtures thereof.

7. The anhydrous antiperspirant composition of claim 1, wherein the beta-cyclodextrin complex consists of beta-cyclodextrins having particle sizes of less than 50 microns.

8. The anhydrous antiperspirant composition of claim 1, comprising from about 0.1% to about 25% of the beta-cyclodextrins, by weight of the composition.

9. The anhydrous composition of claim 1, wherein the secondary fragrance comprises one or more Class 2 High Impact Accord (HIA) perfume ingredients, wherein Class 2 HIA ingredients have a boiling point of greater than 275° C. at a normal, standard pressure of about 760 mm Hg.

10. The anhydrous antiperspirant composition of claim 9, wherein the secondary fragrance comprises one or more Class 1 HIA ingredients, wherein Class 1 HIA ingredients have boiling point less than about 275° C. at a normal, standard pressure of about 760 mm Hg.

11. The anhydrous antiperspirant composition of claim 10, wherein the secondary fragrance comprises from 0.01% to about 75% by weight of Class 1 HIA ingredients and Class 2 HIA ingredients.

12. The anhydrous antiperspirant composition of claim 10, wherein the secondary fragrance comprises from 0.01% to about 25% by weight of Class 2 HIA ingredients.

13. The anhydrous antiperspirant composition of claim 10, wherein the secondary fragrance comprises from about 15% to about 50% by weight of Class 1 HIA ingredients.

14. The anhydrous antiperspirant composition of claim 1, wherein the secondary fragrance comprises no perfume chemicals that are included in the primary fragrance.

* * * * *